US010360892B2

(12) United States Patent
Lee et al.

(10) Patent No.: US 10,360,892 B2
(45) Date of Patent: Jul. 23, 2019

(54) SPECTRAL OPTIMIZATION OF AUDIO MASKING WAVEFORMS

(71) Applicant: Bose Corporation, Framingham, MA (US)

(72) Inventors: Daniel K. Lee, Framingham, MA (US); Daniel M. Gauger, Jr., Berlin, MA (US); Aric J. Wax, Watertown, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 15/616,411

(22) Filed: Jun. 7, 2017

(65) Prior Publication Data

US 2018/0357995 A1 Dec. 13, 2018

(51) Int. Cl.

| | |
|---|---|
| ***A61F 11/06*** | (2006.01) |
| ***G10K 11/178*** | (2006.01) |
| ***H04R 1/10*** | (2006.01) |
| ***G10L 25/18*** | (2013.01) |
| ***G10K 11/175*** | (2006.01) |
| *H04R 3/00* | (2006.01) |

(52) U.S. Cl.

CPC .......... *G10K 11/178* (2013.01); *G10K 11/175* (2013.01); *G10L 25/18* (2013.01); *H04R 1/1083* (2013.01); *G10K 2210/1081* (2013.01); *G10K 2210/3011* (2013.01); *G10K 2210/3028* (2013.01); *H04R 3/00* (2013.01); *H04R 2420/07* (2013.01)

(58) Field of Classification Search

CPC ....... G10K 11/1782; G10K 2210/1081; G10K 2210/3011; G10K 2210/3028; G10L 25/18; H04R 1/1083

USPC ................................................ 381/71.1–73.1

See application file for complete search history.

(56) References Cited

U.S. PATENT DOCUMENTS

| | | | | | |
|---|---|---|---|---|---|
| 6,487,529 | B1 * | 11/2002 | Miet | H04R 3/00 | 704/205 |
| 8,472,616 | B1 * | 6/2013 | Jiang | H04M 9/082 | 370/286 |
| 2003/0179820 | A1 * | 9/2003 | Bombard | G01R 23/16 | 375/224 |
| 2004/0032796 | A1 | 2/2004 | Chu et al. | | |
| 2010/0278353 | A1 * | 11/2010 | Taenzer | H04R 1/1083 | 381/73.1 |

(Continued)

OTHER PUBLICATIONS

International Search Report and Written Opinion dated Sep. 27, 2018 for International application No. PCT/US2018/036313.

*Primary Examiner* — Xu Mei
*Assistant Examiner* — Ammar T Hamid
(74) *Attorney, Agent, or Firm* — Bose Corporation

(57) ABSTRACT

A system for masking audio signals includes a microphone for generating an ambient audio signal representing ambient noise, a speaker for rendering masking audio, and a processor in communication with the microphone and the speaker. The processor performs spectral analysis on the ambient audio signal from the microphone to determine a spectral envelope of the ambient noise, adjusts a frequency response of an optimizing filter based on the spectral envelope, applies the optimizing filter to a baseline masking waveform, producing an output waveform with relative spectral distribution matching the ambient noise, and provides the output waveform to the speaker.

15 Claims, 3 Drawing Sheets

(56) References Cited

U.S. PATENT DOCUMENTS

| | | | | |
|---|---|---|---|---|
| 2011/0228951 | A1* | 9/2011 | Sekiya | G10L 21/0208 381/94.1 |
| 2011/0235813 | A1 | 9/2011 | Gauger, Jr. | |
| 2013/0337796 | A1* | 12/2013 | Suhami | H04R 25/00 455/422.1 |
| 2015/0003625 | A1 | 1/2015 | Uhle et al. | |
| 2015/0063573 | A1* | 3/2015 | Daly | H04S 7/302 381/17 |
| 2015/0117660 | A1* | 4/2015 | Fletcher | G10K 11/178 381/72 |
| 2017/0004817 | A1* | 1/2017 | Donaldson | G10K 11/178 |

* cited by examiner

SPECTRAL OPTIMIZATION OF AUDIO MASKING WAVEFORMS

BACKGROUND

Human beings subjected to high ambient acoustic noise environments can suffer a variety of negative effects, such as degraded ability to perform tasks or inability to sleep.

Several techniques exist to reduce the effects of ambient noise. For instance, sound absorbing material can surround the ears or be inserted in the ear canal, typically achieving 20 to 30 dB reduction of external sounds. Passive noise attenuation can be supplemented by combining absorptive materials with an acoustic transducer, such as a miniature speaker. The transducer is used to produce sounds which may be designed to actively cancel residual noise at the ear, or to provide sounds which are designed to conceal the external noise through the psychoacoustic phenomenon of masking, where one sound prevents the perception of another. A masking signal as typically implemented can achieve a total perceived noise suppression of up to 70 dB in combination with sound absorption materials alone or sound absorption plus active cancellation.

The present invention describes a technique for improving the performance of audio waveforms generated specifically for sound masking.

SUMMARY

In general, in one aspect, a system for masking audio signals includes a microphone for generating an ambient audio signal representing ambient noise, a speaker for rendering masking audio, and a processor in communication with the microphone and the speaker. The processor performs spectral analysis on the ambient audio signal from the microphone to determine a spectral envelope of the ambient noise, adjusts a frequency response of an optimizing filter based on the spectral envelope, applies the optimizing filter to a baseline masking waveform, producing an output waveform with relative spectral distribution matching the ambient noise, and provides the output waveform to the speaker.

Implementations may include one or more of the following, in any combination. The processor may adjust the level of sound output by the speaker to maximize perceived suppression of external noise sources by the rendered masking audio. The processor may apply a non-adaptive equalization filter to the output waveform before providing the equalized output waveform to the speaker. The processor may perform the spectral analysis by amplifying the ambient audio signal, applying an array of bandpass filters with center frequencies distributed across the audio band to the amplified signal, producing bandpass-filtered signals, measuring the magnitude of the bandpass-filtered signals from each bandpass filter, combining the measured output magnitudes to form a spectral mask of the ambient noise over the audio band, and normalizing and scaling the spectral mask to generate adjustment coefficients of the optimizing filter. The processor may apply the array of bandpass filters by applying digital IIR or FIR filters to the amplified signal. The processor may apply the array of bandpass filters by repeatedly applying an adjustable bandpass filter to the amplified signal, with the center frequency changing for each application.

The processor may perform the spectral analysis by applying a discrete fast-Fourier transform (DFFT) to a digital representation of the ambient audio signal, the DFFT output consisting of a plurality of frequency bins, using the values in the DFFT output bins as representations of the magnitude of the ambient sound in each of a plurality of frequency bands corresponding to the frequency bins, combining the magnitudes to form a spectral mask of the ambient noise over the audio band, and normalizing and scaling the spectral mask to generate adjustment coefficients of the optimizing filter. The spectral analysis may be performed over a sampling interval of between 10 and 300 seconds. The spectral analysis may be performed over a sampling interval of between 20 and 30 seconds. The processor may repeat the spectral analysis, frequency response adjustment, and application of the optimizing filter on a periodic basis. The periodic basis may be every five minutes. The output of each repetition of the application of the optimizing filter may be combined with previous results to produce a long-term composite measurement. The long-term composite measurement of analysis performed over at least a first night may be used to produce an output waveform for use on subsequent nights. The processor may provide the output waveform to the speaker by storing the output waveform in a memory, and retrieving the output waveform from the memory and providing it to an amplifier coupled to the speaker. The processor may provide the output waveform to the speaker by providing the output waveform to an amplifier coupled to the speaker as the output waveform may be generated.

One or more of the processor tasks may be performed by a portable computing device. The microphone may be a component of the portable computing device, and the speaker may be a component of an earbud in wireless communication with the portable computing device. The microphone may be external to the portable computing device. The microphone and the speaker may be components of an earbud in wireless communication with the portable computing device. One or more of the processor tasks may be performed by the portable computing device, results of those tasks being transferred to the earbud, the remainder of the processor tasks being performed in the earbud. The spectral analysis and the adjusting of the frequency response of the optimizing filter may be performed in the portable computing device, the adjustment to the optimizing filter may be provided to the earbud, and the application of the filter may be performed in the earbud. The processor, microphone, and speaker may be components of an earbud. The earbud may be in wireless communication with a portable computing device, the portable computing device providing a user interface for configuring the processor of the earbud. The processor may adjust the frequency response of the optimizing filter and apply the optimizing filter to the baseline masking waveform by activating one or more switches to direct a signal representing the baseline masking waveform to a selected one of a set of optimizing filters, and to direct output of the selected optimizing filter to the speaker.

In general, in one aspect, masking audio signals includes receiving an ambient audio signal representing ambient noise from a microphone, performing spectral analysis on the ambient audio signal from the microphone to determine a spectral envelope of the ambient noise, adjusting a frequency response of an optimizing feature based on the spectral envelope, applying the optimizing filter to a baseline masking waveform, producing an output waveform with relative spectral distribution matching the ambient noise, and providing the output waveform to a speaker.

Implementations may include one or more of the following, in any combination. The spectral analysis may include applying a discrete fast-Fourier transform (DFFT) to a digital representation of the ambient audio signal, the DFFT output consisting of a plurality of frequency bins, using the values in the DFFT output bins as representations of the magnitude of the ambient sound in each of a plurality of frequency bands corresponding to the frequency bins, combining the magnitudes to form a spectral mask of the ambient noise over the audio band, and normalizing and scaling the spectral mask to generate adjustment coefficients of the optimizing filter.

DETAILED DESCRIPTION

Generation of Masking Waveforms or Tones

Various artificial or natural sounds are effective for noise masking. For example, natural sounds such as rainfall, ocean waves and water flowing in streams or rivers have been used. An example of an artificial masking sound is the use of generated random noise, where the distribution of the noise over the human hearing frequency range (typically considered as 20 Hz to 20 kHz) can be for example white noise (constant energy per unit of frequency) or pink noise (constant energy per unit log frequency or octave). In these simple examples, the frequency or spectral distribution of the masking sound is fixed during creation of the waveform, and therefore does not take into account the specific characteristics of the ambient external noise environment.

As currently implemented, the masking waveform is delivered to the audio transducer located in or near the ears, and its amplitude level or loudness is adjusted to provide an acceptable level of perceived ambient noise suppression. Setting of the relative loudness of the delivered masking sound is a critical aspect of the performance of the method, since insufficient levels may not deliver adequate perceived noise suppression, while excessive levels may result in the masking sounds being objectionable themselves.

The present invention optimizes the performance of masking waveforms by matching the spectral distribution of sound energy to that of the ambient noise environment, thus allowing the masking sound level at the output transducer to be adjusted for maximum suppression effectiveness while avoiding excessive levels.

Figure 1:
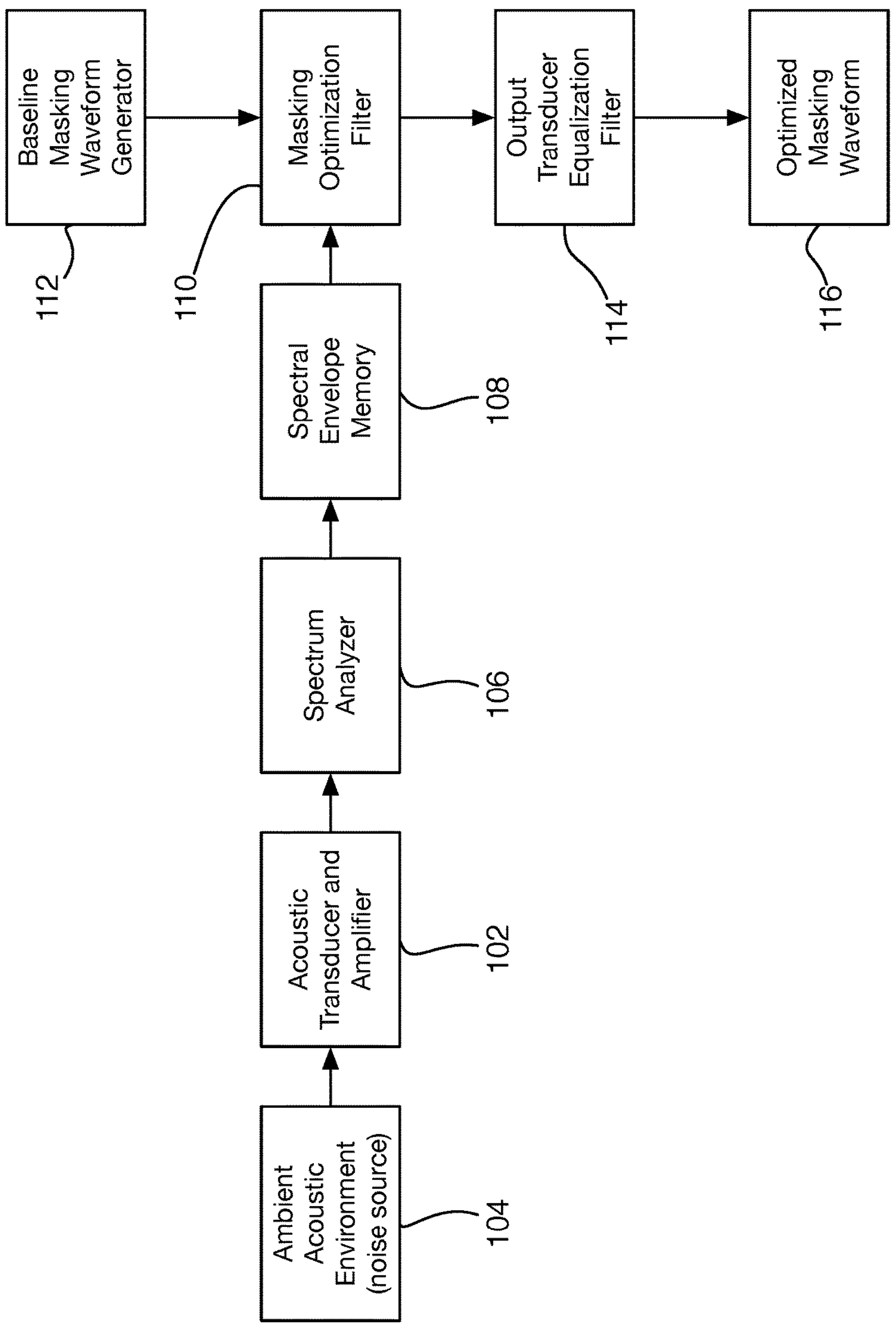
FIGS. 1, 2, and 3 show block diagrams of systems for optimizing audio masking waveforms.

FIG. 1 illustrates the general system. An audio transducer 102, for example a microphone, is positioned in the ambient sound environment 104, and a spectral analysis is performed (106) on its output. The spectral envelope of the ambient noise is determined (108) and used to adjust the frequency response of an optimizing filter 110, through which the baseline masking waveform (112) is then passed, resulting in an output waveform with relative spectral distribution matching the external ambient noise. The masking waveform 112 may be generated or may be a stored file which is played back and looped. In some examples, a small set of pre-configured filters are available, with simple analog switching used to route the audio signal through the filter that best matches the noise. A further, non-adaptive, equalization filter 114 may then be used to compensate for spectral response of an output transducer, for example a speaker element, as well as any other equalization appropriate to the use which is common to all settings of optimizing filter 110. The composite masking waveform 116 is then delivered to the output transducer. Adjustment of the sound level at the ear is performed to achieve maximum perceived suppression of external noise sources.

Figure 2:
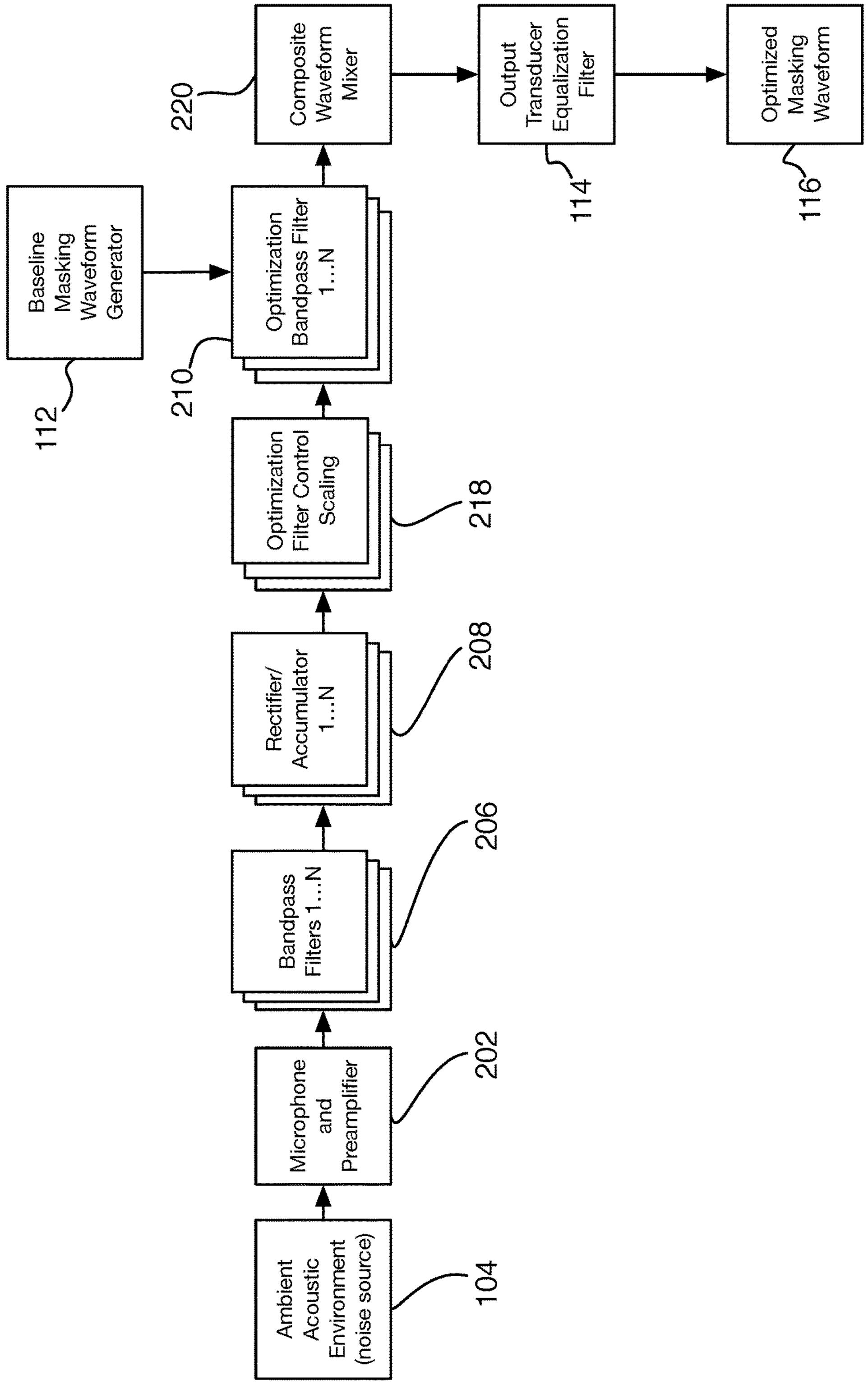

FIG. 2 illustrates a first example implementation of the method. A measurement microphone 202 is positioned near or at the listening location, and its output is amplified to a level suitable for spectral analysis. The ambient sound waveform is then input to an array 206 of N bandpass filters with center frequencies distributed across the audio band.

The bandpass filters may be realized using various implementations. For example they could consist of analog active or passive filters. Another example is the use of digital IIR or FIR filters or a Discrete Fourier Transform. Another example is the use of a single adjustable bandpass filter where the center frequency is swept over the audio band, either directly or by using frequency conversion of the input band.

The output magnitude of each filter is measured and combined (208) to form a spectral mask of the environmental noise over the audio band. The spectral mask is then normalized and scaled (218) to form the adjustment coefficients of the output optimizing filter 210. Similar to the input filters, the output filter can be realized using any of the methods previously presented.

The masking waveform is then generated or played back (112) and fed through the optimization and equalization filters 210, the output of which is then mixed (220) and delivered to the output transducer (114, 116). The output waveform may be delivered using a variety of techniques. For example it could be stored in a file for later playback or delivered directly to the output transducer after appropriate amplification.

Figure 3:
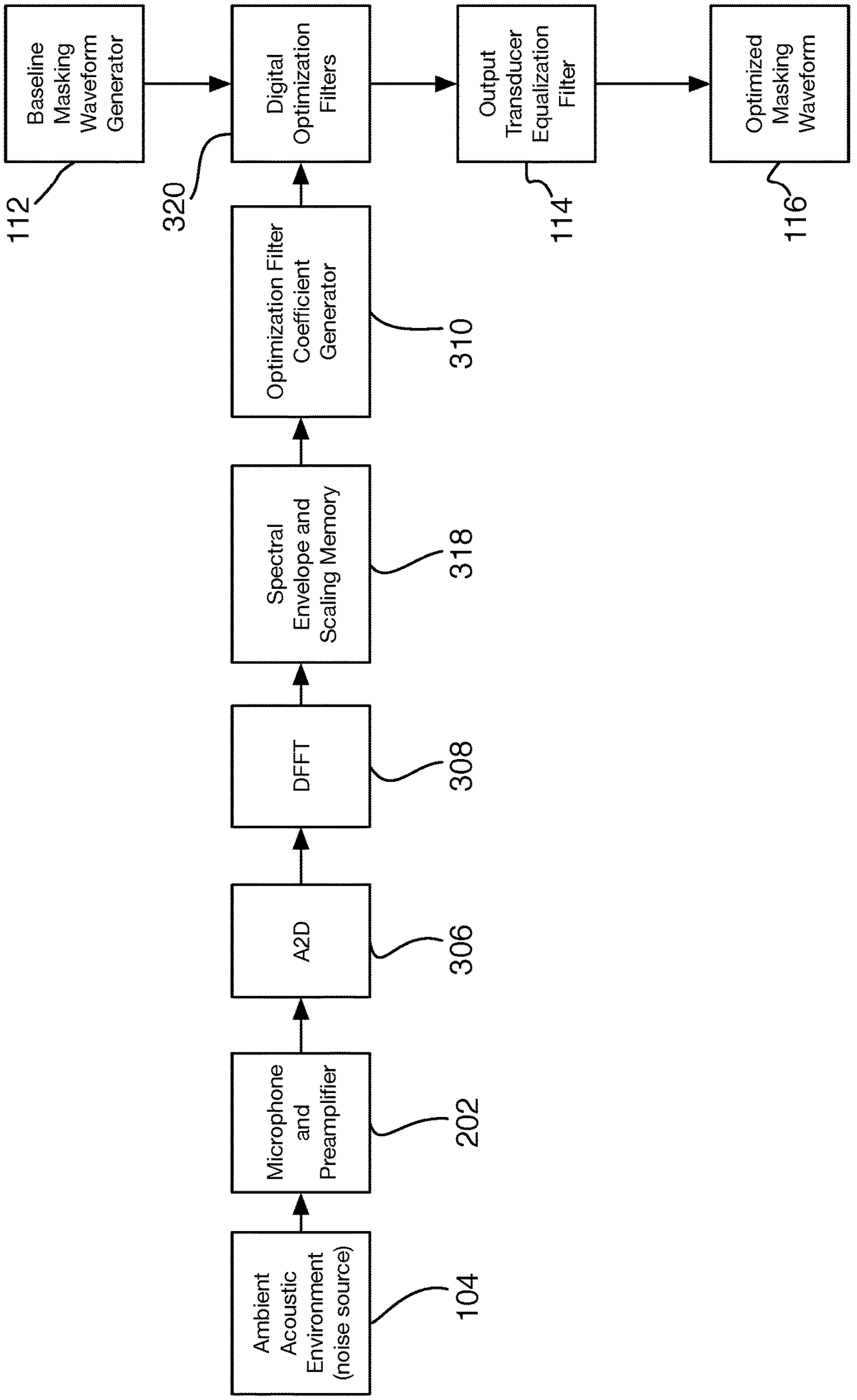

FIG. 3 illustrates a realization of the method using a generalized computing platform to perform the required signal processing. Possible computing platforms include, but are not limited to, devices such as smartphones, tablets, or conventional personal computers.

In this realization, the input transducer is positioned near the listening position. If a microphone is used, it may be contained within the computing platform, for example, within a smartphone. Alternatively an external microphone could be attached, potentially providing improved frequency response and directivity more suited to the masking application as compared to the device's embedded microphone.

The transducer output is amplified and directed to an analog-to-digital converter 306, whose output is then processed through a discrete fast-Fourier transform (DFFT) algorithm 308. The DFFT output consists of N frequency bins which are equivalent to a bank of parallel bandpass filters. Each bin contains a value proportional to the magnitude of ambient sound energy in its equivalent bandwidth around each equivalent filter center frequency.

The measured spectral envelope is normalized and scaled (318) to derive coefficients 310 used adjust the output digital filter bank 320 to the optimized spectral envelope. The baseline masking waveform 112 is directed to the inputs of the optimization filters. Outputs from the optimization filters are summed and directed to the transducer equalization filter 114, after which the optimized masking waveform file 116 is generated and stored in a standard audio file.

As previously discussed, the optimized waveform can be delivered to the target output transducer using one of several methods such as a stored file transfer or via an appropriate communication and amplification process. For example, the analysis to determine the optimization (104 through 310 in FIG. 3) could be done in a device whereas generation or playback of a stored baseline masking waveform (112) and its subsequent equalization (320 and 114) are done in the user-worn earpieces. The coefficients describing the optimization passed from 310 to 320 can be communicated by various means such as Bluetooth. Since changing masking should be done very slowly so that the changes in the sound of the masking are not in themselves distracting, the bandwidth and power requirements needed to support that communication is very small.

The realization shown in FIG. 3 would be implemented on a smartphone, running application software designed to perform the required signal processing functions. This platform has several advantages in the end application of the system. These advantages include, but are not limited to:

1. The platform is widely available, and the end user likely will already have a compatible device.
2. All required hardware and computing resources are contained within a small, portable device which can quickly be positioned at or near the listening position.
3. The system output shown in FIG. 3 would consist of an audio playback file compatible with user-worn earpieces designed specifically for noise suppression. The smartphone platform also provides the communication hardware and protocol required to wirelessly transfer the file to the target device or to communicate equalization parameters to a much more limited-in-capability equalization process running in the target device.
4. The included communication capability, such as Bluetooth, and application software provides for user interaction and control of the earpiece device. For example, the user can enable or disable playback of the masking waveform, or the earpiece can notify the user of battery status or other operational parameters.
5. Application software can be easily installed and updated via an internet connection.
6. The application software can be designed to perform various tasks or processes on a scheduled basis.
7. Interfaces, such as USB and a microphone/earpiece connector, are provided for attachment of external devices which may enhance the performance of the system.

In the envisioned operation of the present invention, in combination with existing noise suppression earpieces, (the product), an end-user would run the application software which was previously installed on a smartphone. The primary intended purpose of the product is to provide suppression of ambient noise during sleep, so the user would thus place the smartphone at the intended sleeping position, such as on a pillow, and then initiate a measurement of the ambient sound environment via an application control. This initiation may be manual or may automatically start if the user wishes when masking is turned on.

Using its internal microphone as the input transducer, the process shown in FIG. 3 would be performed over some sampling interval Ts, where the sampling interval might have a default value of 10 seconds but allow for different intervals to selected by the user. Values of 20 to 30 seconds, or as long as 300 seconds (five minutes) may be desirable. For example, a longer measurement might be desired if the end user observes that a periodic transient noise source is present which might not be captured in a short interval. While rapid response to a transient noise can be just as disruptive as the noise, a sampling period that captures it may result in a long-term masking signal that successfully masks the transient noise. Alternatively, the noise measurement process (104 through 308) may run continuously and then averaging of the noise spectrum over time is done as part of 318. This averaging may be designed to provide the average energy of the noise or to respond to short transients in the noise. At the completion of the spectral characterization process, the optimized masking waveform file would be downloaded automatically to the earpiece(s) or the optimization parameters transferred. The user would then install the earpieces and activate playback of the file via the control aspect of the application software at the appropriate time.

A single characterization of the ambient sound environment will provide excellent masking performance if external noise sources are relatively invariant. However, it is not unreasonable to expect certain noises, such as a partner's snoring or various household appliances, to stop or start during a sleep period. Therefore, the application software could be configured to automatically perform the measurement process at regular intervals, such as every five minutes. The spectral parameters associated with the current version of the optimized waveform would be stored in memory, and new measured parameters would be compared with them and a determination made as to whether significant ambient changes have occurred. If sufficient change is detected, a new optimized waveform file would be generated and automatically transferred to the earpieces for playback. In other examples, a long-term average may be used, with measurements taken throughout the night, but the filters updated only after the full night, or several nights, has been recorded. In this way, a fixed filter, which doesn't react to short-term changes, but does mask all the typical noises in the environment, may be used.

The automated re-optimization process would require that the smartphone, with its internal microphone, remain positioned near the user's head over the sleep period. This could be inconvenient or undesirable to the user. Using the headset connector of the smartphone or a wireless connection, an external microphone could be used instead. The accessory microphone can be much smaller than the smartphone, thus providing better options for positioning it in a convenient and undisturbed location near the user's head.

An external microphone can also provide enhanced measurement performance. For example, the smartphone microphone is designed to perform optimally for capturing the voice audio band, and is intentionally directional to provide suppression of undesired sound during voice calls. Frequency response shaping of the internal microphone and its directionality can each result in some degradation of accuracy in the ambient sound spectral measurement. However, it is possible to provide additional equalization parameters at the optimization filter of FIG. 3 to compensate for a typical internal microphone response, but the effect of directionality depends on the position of the phone during the measurement and its spatial orientation relative to ambient noise sources. External microphones with non-directional characteristics and relatively flat frequency response are readily available, and if used instead of the internal smartphone microphone, would substantially improve the accuracy of an ambient sound measurement.

An additional benefit of an external microphone is that its response can be calibrated in terms of sound pressure level (SPL), a widely used parameter for measurements related to sound. If the measured spectral envelope is in terms of SPL, this allows the system of FIG. 3 to estimate the average actual sound incident on the earpiece elements. Given knowledge of the noise attenuation response of the earpiece in the ear, a good estimate of the playback volume setting for the masking waveform in the earpiece can be made and transferred to the earpiece along with the optimized file. Thus, user interaction with the playback level setting can be minimized in most circumstances.

The foregoing description illustrates exemplary implementations, and novel features, of aspects of a system, method and apparatus for spectral optimization of audio masking waveforms. Alternative implementations are suggested, but it is impractical to list all alternative implementations of the present teachings. Therefore, the scope of the presented disclosure should be determined only by reference to the appended claims, and should not be limited by features illustrated in the foregoing description except insofar as such limitation is recited in an appended claim.

While the processes described result in a masking signal, as delivered to the ear, which is adapted to match changes in the ambient noise environment to most effectively mask them while still being played quietly, matching the environment may not be the best choice in terms of creating a pleasant and sleep-facilitating experience for the user. For this reason, the optimization filter control (218 or 310) may in addition include rules that prevent the optimized masking signal from taking on an annoying quality. These may include, for example, broadening of narrow-band peaks that may have been measured in the ambient acoustic environment (such as might be caused by a squeaking fan) or to ensure that ratio of low to mid to high frequencies does not skew too much from what is deemed pleasant. In this example, if the system measures a substantial increase in broad high-frequency noise, rather than making the masking unpleasantly harsh and bright it is better to increase energy at lower frequencies in balance with the higher frequencies.

While the above description has pointed out novel features of the present disclosure as applied to various embodiments, the skilled person will understand that various omissions, substitutions, permutations, and changes in the form and details of the present teachings illustrated may be made without departing from the scope of the present teachings.

Each practical and novel combination of the elements and alternatives described hereinabove, and each practical combination of equivalents to such elements, is contemplated as an embodiment of the present teachings. Because many more element combinations are contemplated as embodiments of the present teachings than can reasonably be explicitly enumerated herein, the scope of the present teachings is properly defined by the appended claims rather than by the foregoing description. All variations coming within the meaning and range of equivalency of the various claim elements are embraced within the scope of the corresponding claim. Each claim set forth below is intended to encompass any apparatus, system, method, or article of manufacture that differs only insubstantially from the literal language of such claim, as long as such apparatus, system, method, or article of manufacture is not, in fact, an embodiment of the prior art. To this end, each described element in each claim should be construed as broadly as possible, and moreover should be understood to encompass any equivalent to such element insofar as possible without also encompassing the prior art. Furthermore, to the extent that the term "includes" is used in either the detailed description or the claims, such term is intended to be inclusive in a manner similar to the term "comprising."

What is claimed is:

1. A system for masking audio signals, the system comprising:

a microphone for generating an ambient audio signal representing ambient noise;

a speaker for rendering masking audio;

a processor in communication with the microphone and the speaker, and configured to:

store a measurement of the ambient audio signal from the microphone;

perform spectral analysis on the stored ambient audio signal to determine a spectral envelope of the ambient noise, based on the spectral envelope, adjust a frequency response of an optimizing filter, apply the optimizing filter to a baseline masking waveform, producing an output waveform with relative spectral distribution matching the ambient noise, and provide the output waveform to the speaker, wherein, the step of storing the measurement of the ambient audio signal is repeated on a periodic basis and averaged over a first time period to produce a long-term composite measurement, the spectral analysis, frequency response adjustment, and application of the optimizing filter to produce the output waveform is performed on a long-term composite measurement of the ambient audio signal, wherein the periodic basis is every five minutes.

2. A system for masking audio signals, the system comprising:

a microphone for generating an ambient audio signal representing ambient noise;

a speaker for rendering masking audio;

a processor in communication with the microphone and the speaker, and configured to:

store a measurement of the ambient audio signal from the microphone;

perform spectral analysis on the stored ambient audio signal to determine a spectral envelope of the ambient noise, based on the spectral envelope, adjust a frequency response of an optimizing filter, apply the optimizing filter to a baseline masking waveform, producing an output waveform with relative spectral distribution matching the ambient noise, and provide the output waveform to the speaker, wherein, the step of storing the measurement of the ambient audio signal is repeated on a periodic basis and averaged over a first time period to produce a long-term composite measurement, the spectral analysis, frequency response adjustment, and application of the optimizing filter to produce the output waveform is performed on a long-term composite measurement of the ambient audio signal, wherein the long-term composite measurement of the ambient audio signal over at least a first night is used to produce an output waveform for use on subsequent nights.

3. The system of claim 1, wherein one or more of the processor tasks are performed by a portable computing device, results of those tasks being transferred to an earbud, the remainder of the processor tasks being performed in the earbud.

4. The system of claim 3, wherein the spectral analysis and the adjusting of the frequency response of the optimizing filter are performed in the portable computing device, the adjustment to the optimizing filter is provided to the earbud, and the application of the filter is performed in the earbud.

5. A method of masking audio signals, the method comprising:

receiving an ambient audio signal representing ambient noise from a microphone;

storing a measurement of the ambient audio signal from the microphone;

performing spectral analysis on the stored ambient audio signal to determine a spectral envelope of the ambient noise;

based on the spectral envelope, adjusting a frequency response of an optimizing feature;

applying the optimizing filter to a baseline masking waveform, producing an output waveform with relative spectral distribution matching the ambient noise; and providing the output waveform to a speaker;

wherein, the step of storing the measurement of the ambient audio signal is repeated on a periodic basis and averaged over a first time period to produce a long-term composite measurement, the spectral analysis, frequency response adjustment, and application of the optimizing filter to produce the output waveform is performed on a long-term composite measurement of the ambient audio signal, wherein the periodic basis is every five minutes.

6. The method of claim 5, wherein performing the spectral analysis comprises:

applying a discrete fast-Fourier transform (DFFT) to a digital representation of the long-term average ambient audio signal, the DFFT output consisting of a plurality of frequency bins;

using the values in the DFFT output bins as representations of the magnitude of the ambient sound in each of a plurality of frequency bands corresponding to the frequency bins;

combining the magnitudes to form a spectral mask of the ambient noise over the audio band; and normalizing and scaling the spectral mask to generate adjustment coefficients of the optimizing filter.

7. A method of masking audio signals, the method comprising:

receiving an ambient audio signal representing ambient noise from a microphone;

storing a measurement of the ambient audio signal from the microphone;

performing spectral analysis on the stored ambient audio signal to determine a spectral envelope of the ambient noise;

based on the spectral envelope, adjusting a frequency response of an optimizing feature;

applying the optimizing filter to a baseline masking waveform, producing an output waveform with relative spectral distribution matching the ambient noise; and providing the output waveform to a speaker;

wherein, the step of storing the measurement of the ambient audio signal is repeated on a periodic basis and averaged over a first time period to produce a long-term composite measurement, the spectral analysis, frequency response adjustment, and application of the optimizing filter to produce the output waveform is performed on a long-term composite measurement of the ambient audio signal, wherein the long-term composite measurement of the ambient audio signal over at least a first night is used to produce an output waveform for use on subsequent nights.

8. The method of claim 5, wherein one or more of the steps are performed by a portable computing device, and results of those tasks are transferred to an earbud, the remainder of the processor tasks being performed in the earbud.

9. The method of claim 5, wherein the spectral analysis and the adjusting of the frequency response of the optimizing filter are performed in the portable computing device, the adjustment to the optimizing filter is provided to the earbud, and the application of the filter is performed in the earbud.

10. The system of claim 2, wherein the optimizing filter is a fixed filter that is updated after the first night, such that the optimizing filter does not react to short-term changes in a listening environment but does mask typical noises in the listening environment.

11. The method of claim 7, wherein the optimizing filter is a fixed filter that is updated after the first night, such that the optimizing filter does not react to short-term changes in a listening environment but does mask typical noises in the listening environment.

12. The system of claim 2, wherein one or more of the processor tasks are performed by a portable computing device, results of those tasks being transferred to an earbud, the remainder of the processor tasks being performed in the earbud.

13. The system of claim 12, wherein the spectral analysis and the adjusting of the frequency response of the optimizing filter are performed in the portable computing device, the adjustment to the optimizing filter is provided to the earbud, and the application of the filter is performed in the earbud.

14. The method of claim 7, wherein one or more of the steps are performed by a portable computing device, and results of those tasks are transferred to an earbud, the remainder of the processor tasks being performed in the earbud.

15. The method of claim 7, wherein the spectral analysis and the adjusting of the frequency response of the optimizing filter are performed in the portable computing device, the adjustment to the optimizing filter is provided to the earbud, and the application of the filter is performed in the earbud.

* * * * *